United States Patent [19]

Torii et al.

[11] Patent Number: 4,609,438

[45] Date of Patent: Sep. 2, 1986

[54] PROCESS FOR PREPARING THIOSULFONATE DERIVATIVES

[75] Inventors: Sigeru Torii; Hideo Tanaka, both of Okayama; Michio Sasaoka; Seiryu Uto, both of Tokushima; Yutaka Kameyama, Okayama, all of Japan

[73] Assignee: Otsuka Kagaku Kabushiki Kaisha, Osaka, Japan

[21] Appl. No.: 673,309

[22] Filed: Nov. 20, 1984

[30] Foreign Application Priority Data

Nov. 25, 1983 [JP] Japan .................. 58-222969

[51] Int. Cl.$^4$ .................................. C25B 3/00
[52] U.S. Cl. .................. 204/72; 204/59 R
[58] Field of Search ................ 204/72, 59 R

[56] References Cited

U.S. PATENT DOCUMENTS 3,786,063  1/1974  Arnold ........................... 260/306.5
4,461,897  7/1984  Cobb et al. ..................... 204/59 R

OTHER PUBLICATIONS

Oae et al., New Syntheses of Thionitrites and Their Chemical Reactivities, J. C. S. Perkin I, 913 (1978).
Weidner et al., Trifluoromethyl Thiolsulfonates and Their Reactions with Mercaptans and Amines, J. Med. Chem., 10, 1167 (1967).

*Primary Examiner*—R. L. Andrews
*Attorney, Agent, or Firm*—Armstrong, Nikaido, Marmelstein & Kubovcik

[57] ABSTRACT

This invention provides a process for preparing a thiosulfonate derivative represented by the formula $$R^2SO_2SR^1 \tag{III}$$

wherein $R^1$ is substituted or unsubstituted 2-benzothiazolyl, and $R^2$ is substituted or unsubstituted phenyl, the process being characterized in that a compound represented by the formula $$R^1SX \tag{I}$$

wherein $R^1$ is as defined above, and X is hydrogen, alkali metal or $SR^1$, and a sulfinic acid or a salt thereof represented by the formula $$R^2SO_2Y \tag{II}$$

wherein $R^2$ is as defined above, and Y is a hydrogen atom, alkali metal atom, alkaline earth metal atom or quaternary ammonium are subjected to an electrolytic reaction in a mixture of water and an organic solvent in the presence of a halogen salt.

12 Claims, No Drawings

PROCESS FOR PREPARING THIOSULFONATE DERIVATIVES

This invention relates to a process for preparing thiosulfonate derivatives, and more particularly to a novel process for preparing thiosulfonate derivatives represented by the formula $$R^2SO_2SR^1 \qquad (III)$$

wherein $R^1$ is substituted or unsubstituted 2-benzothiazoyl, and $R^2$ is substituted or unsubstituted phenyl.

The thiosulfonate derivative represented by the formula (III) is a known compound which is useful as a vulcanization accelerator for rubbers and also as a reaction reagent.

The processes heretofore known for preparing the compound of the formula (III) include, for example, the process disclosed in U.S. Pat. No. 3,786,063. This process is represented by the following reaction formula $$R^1SSR^1 \xrightarrow{Cl_2} R^1SCl \xrightarrow{R^2SO_2Na} R^1SSO_2R^2$$

wherein $R^1$ and $R^2$ are as defined above. However, the process involves formation of sulfenyl chloride which is an unstable intermediate, so that special consideration must be given to the reaction procedure. Moreover, the process has the drawback that the yield of the desired compound of the formula (III) is up to about 70%.

An object of the present invention is to provide a process for preparing the thiosulfonate compound in a high yield.

Another object of the invention is to provide a process for preparing the thiosulfonate compound without involving the formation of unstable sulfenyl chloride.

These objects and other features of the invention will become more apparent from the following description.

The present invention provides a process for preparing a thiosulfonate derivative represented by the formual $$R^2SO_2SR^1 \qquad (III)$$

wherein $R^1$ is substituted or unsubstituted 2-benzothiazolyl, and $R^2$ is substituted or unsubstituted phenyl, the process being characterized in that a compound represented by the formula $$R^1SX \qquad (I)$$

wherein $R^1$ is as defined above, and X is hydrogen, alkali metal or $SR^1$, and a sulfinic acid or a salt thereof represented by the formula $$R^2SO_2Y \qquad (II)$$

wherein $R^2$ is as defined above, and Y is a hydrogen atom, alkali metal atom, alkaline earth metal atom or quaternary ammonium are subjected to an electrolytic reaction in a mixture of water and an organic solvent in the presence of a halogen salt.

According to the present process, the desired thiosulfonate derivative of the formula (III) can be prepared by a simple procedure in a high yield of at least 80% or substantially quantitative high yield. The present process requires no special consideration because unstable sulfenyl chloride is not used as a material or intermediate, and is therefore industrially advantageous.

Examples of substituents for 2-benzothiazolyl represented by $R^1$ and for phenyl represented by $R^2$ are $C_1$–$C_4$ alkyl groups such as methyl, ethyl, propyl, isopropyl, butyl and tert-butyl; $C_1$–$C_4$ alkoxyl groups such as methoxy, ethoxy, propoxy, isopropoxy, butoxy and tert-butoxy; nitro; hydroxyl; $C_2$–$C_4$ alkanoyloxy groups such as acetoxy, ethylcarbonyloxy and propylcarbonyloxy; $C_2$–$C_4$ alkoxycarbonyl groups such as methoxycarbonyl, ethoxycarbonyl and propoxycarbonyl; amino; $C_2$–$C_5$ alkylcarbonylamino groups such as methylcarbonylamino, ethylcarbonylamino, propylcarbonylamino and butylcarbonylamino; halogen atoms such as fluorine, chlorine, bromine and iodine atoms; etc.

The thiols, mercaptides or disulfides of the formula (I), and the sulfinic acis or salts thereof of the formula (II), which are used as starting materials in the present invention, are all known compounds. Typical examples of groups represented by $R^1$ in the compounds of the formula (I) are benzothiazol-2-yl, 4-methylbenzothiazol-2-yl, 6-methylbenzothiazol-2-yl, 4,6-dimethylbenzothiazol-2-yl, 5-methoxybenzothiazol-2-yl, 6-nitrobenzothiazol-2-yl, 5-chlorobenzothiazol-2-yl, 6-chlorobenzothiazol-2-yl, 6-hydroxybenzothiazol-2-yl, 4-hydroxybenzothiazol-2-yl, 6-acetoxybenzothiazol-2-yl, 4-acetoxybenzothiazol-2-yl, 5-methoxycarbonylbenzothiazol-2-yl, 6-methoxycarbonylbenzothiazol-2-yl, 5-methylcarbonylaminobenzothiazol-2-yl, etc. Typical examples of groups represented by $R^2$ in the compounds of the formula (II) are phenyl, p-tolyl, p-bromophenyl, p-chlorophenyl, p-nitrophenyl, o-nitrophenyl, p-methoxyphenyl, 3,4,5-trimethoxyphenyl, 3,5-dimethoxy-4-hydroxyphenyl, 2,4-dinitrophenyl, 2,4,6-trimethoxyphenyl, p-acetoxyphenyl, p-aminophenyl, p-methoxycarbonylphenyl, etc. Examples of atoms represented by Y are alkali metal atoms such as sodium, potassium and lithium and alkaline earth metal atoms such as magnesium, calcium, barium, and strontium. Examples of quaternary ammonium groups represented by Y are ammonium; tetra($C_1$–$C_8$ alkyl)ammonium groups such as tetramethylammmonium, tetraethylammonium and tetrabutylammonium; tetraarylammonium such as tetraphenylammonium, benzyltri($C_1$–$C_4$ alkyl)ammonium groups, e.g. benzyltriethylammonium, benzyltributylammonium, etc.

Halogen salts useful for the present invention act as supporting electrolyte, and include metal halides or quaternary ammonium halides. Examples of useful metal halides are alkali metal halides such as LiCl, LiBr, LiI, NaCl, NaBr, NaI, KCl, KBr and KI; alkaline earth metal halides such as $MgCl_2$, $MgBr_2$, $MgI_2$, $CaCl_2$, $CaBr_2$, $CaI_2$, $BaCl_2$, $BaBr_2$ and $BaI_2$; and heavy metal halides such as $CuBr_2$, $CuCl_2$, $CoCL_3$, $CoBr_3$ and $FeCl_3$. Further exemplary of useful quaternary ammonium halides are $NH_4Br$, $NH_4Cl$, and halides, such as chlorides, bromides and iodides, of tetra($C_1$–$C_4$ alkyl)ammoniums including tetraethylammonium bromide, tetramethylammonium bromide, tetramethylammonium chloride, etc. The amount of the halogen salt to be used varies with the kind of halogen salt, but is usually about 0.01 to about 10 moles, preferably about 0.1 to about 5 moles, per mole of the compound of the formula (I).

Examples of organic solvents useful for the present invention are di($C_1$–$C_4$ alkyl)ethers such as diethylether; cyclic ethers such as tetrahydrofuran and dioxane; di($C_1$-$C_4$ alkyl)ketones such as acetone, methyl ethyl ketone and diethyl ketone; $C_2$-$C_4$ nitriles such as acetonitrile and propionitrile; $C_1$-$C_4$ aliphatic alcohols such as methanol, ethanol and isopropanol; $C_1$-$C_4$ halogenated hydrocarbons such as dichloromethane, chloroform, bromoform, dichloroethane and dibromoethane; esters of $C_1$-$C_4$ fatty acides with $C_1$-$C_4$ aliphatic alcohols, such as methyl formate, ethyl formate, methyl acetate and ethyl acetate; halogenobenzenes such as chlorobenzene, 1,3-dichlorobenzene, 1,4-dichlorobenzene; etc. These solvents are used singly or in admixture. The amount of organic solvent to be used, which varies with the kind of the compound (I), compound (II) or halogen salt to be used for the reaction, is usually about 5 to about 500 times, preferably about 50 to about 300 times, the amount of compound (I) by weight. The amount of water to be admixed with the organic solvent is usually about 1 to about 50% by weight of the organic solvent, although the optimum amount varies according to the kind of reactants or organic solvent to be used.

The amount of compound (II) to be used is not limited particularly and is suitably variable widely. It is usually at least about 1 equivalent, preferably about 1 to about 3 equivalents based on the compound (I).

The term "equivalent" as herein used is based on the $R^1S$ residue. The expression "1 equivalent" means that one mole of the compound (II) is used per mole of the compound (I) when the compound (I) is represented by the formula $R^1SH$ or $R^1S$ (alkali metal), or that two moles of the compound (II) is used per mole of the compound (I) when the compound (I) is represented by the formula $R^1S$—$SR^1$.

The electrolysis of the present invention may be conducted under the condition of constant voltage, but is usually carried out at a constant current density of about 1 to about 500 mA/cm$^2$, preferably about 5 to about 200 mA/cm$^2$. The amount of current to be passed for the present electrolytic reaction is not definite and varies according to the shape of the electrolytic cell, kind of electrodes, density and reactivity of substrates, reaction temperature, etc. Generally, the amount of electricity is about 1 to about 20 F per mole of the compound of the formula (I). The electrodes to be used are those conventionally used for electrolytic reactions, such as platinum, titanium, carbon, stainless steel, lead oxide, nickel or copper electrodes.

The present electrolytic reaction, which can be carried out at a temperature of about −20 to about +100° C., is conducted preferably at about −10 to about +50° C.

After the completion of electrolysis, the desired compound (III) is obtained by a usual extraction procedure. The product, which need not always be purified, can be purified by a conventional method such as recrystallization or column chromatography.

The invention will be described with reference to the following examples, to which the invention is not limited.

EXAMPLE 1

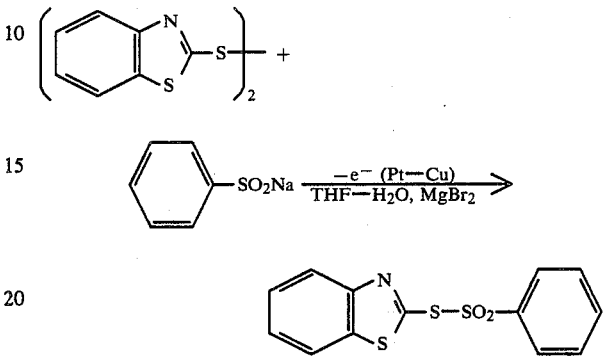

A 49.2 mg quantity of 2-benzothiazolyl disulfide was dissolved in 10 ml of tetrahydrofuran (hereinafter referred to as "THF"). To the solution was added a solution of 58.1 mg of sodium benzenesulfinate and 200 mg of MgBr$_2$. 6H$_2$O in 2 ml of H$_2$O to prepare an electrolyte solution. The solution was subjected to electrolysis in a cell equipped with a platinum anode (3 cm$^2$) and a copper cathode (3 cm$^2$) under the conditions of a constant current density of 10 mA/cm$^2$, terminal voltage of 5 to 9 V and a reaction temperature of 24° to 29° C. After applying 2.9 F of electricity per mole of the 2-benzothiazolyl disulfide, the electrolytic solution was concentrated in a vacuum to about 2 ml by a rotary evaporator, and 10 ml of CHCl$_3$ and 5 ml of H$_2$O were added to the concentrate. Subsequently the organic layer was separated off, washed with saturated common salt solution, and dried with addition of MgSO$_4$. The resulting mass was then concentrated in a vacuum to give a crude product of 2-benzothiazolyl benzenethiosulfonate in the form of a pale yellow solid. The product was subjected to silica gel column chromatography (eluent; benzeneethyl acetate, V/V 20:1), affording 87.3 mg of 2-benzothiazolyl benzenethiosulfate (yield 95.6% based on 2-benzothiazolyldisulfide).

NMR spectrum (CDCl$_3$): δ(ppm) 7.1-8.1 (9H, m)

EXAMPLES 2-6

Following the general procedure of Example 1 and employing the conditions listed in Table 1, 2-benzothiazolyl benzenethiosulfonate was prepared. Table 1 also shows the yield of 2-benzothiazolyl benzenethiosulfonate. The yield (%) is expressed relative to the benzothiazolyl disulfide used.

TABLE 1

| Ex. No. | Substrates mg[1] | Solvents ml | Halogen salt mg | Electrode (+) (−) | Terminal Voltage V | Amount of Electricity F/mole[2] | Yield mg (%) |
|---|---|---|---|---|---|---|---|
| 2 | 49.2 | THF 10 | MgBr$_2$.6H$_2$O | Pt—Cu | 5–9 | 3.8 | 85.4 |
|   | 57.7 | H$_2$O 2 | 200 |   |   |   | (94.0) |
| 3 | 49.7 | Acetone 10 | MgBr$_2$.6H$_2$O | Pt—Cu | 5–9 | 3.7 | 78.0 |
|   | 57.7 | H$_2$O 2 | 200 |   |   |   | (85.0) |
| 4 | 49.2 | Dioxane 10 | MgBr$_2$.6H$_2$O | Pt—Cu | 13 | 6.9 | 78.7 |
|   | 58.1 | H$_2$O 2 | 200 |   |   |   | (86.5) |
| 5 | 49.2 | THF 10 | MgI$_2$.6H$_2$O | Pt—Cu | 6 | 3.0 | 82.0 |
|   | 58.1 | H$_2$O 2 | 264 |   |   |   | (89.8) |
| 6 | 49.2 | THF 10 | CaI$_2$.nH$_2$O | Pt—Cu | 3–4 | 3.8 | 77.9 |

TABLE 1-continued

| Ex. No. | Substrates mg[1] | Solvents ml | Halogen salt mg | Electrode (+)(−) | Terminal Voltage V | Amount of Electricity F/mole[2] | Yield mg (%) |
|---|---|---|---|---|---|---|---|
| | 58.1 | $H_2O$ 2 | 300 | | | | (85.7) |

Note
[1]The upper value is the amount of 2-benzothiazolyl disulfide, and the lower value is the amount of sodium benzenesulfinate.
[2]Amount of electricity passed per mole of the 2-benzothiazolyl disulfide used.

EXAMPLES 7–18

The procedure of Example 1 was repeated except that 2-benzothiazolyl disulfide and sodium benzenesulfinic acid were replaced by the compounds listed in Table 2 below and further with the exception of the electrolysis conditions given in Table 2. The spectrum data of the products are summarized in Table 3. In Table 2, "amount of electricity" is per mole of the compound of the formula (I) used, and "yield (%)" is based on the compound of the formula (I) used.

TABLE 2

| Ex. No. | Substrates mg | Solvents ml | Halogen salt mg | Electrode (+) (−) | Terminal Voltage V | Amount of Electricity F/mole | Product Yield mg (%) |
|---|---|---|---|---|---|---|---|
| 7 | (benzothiazolyl-S-SO$_2$-phenyl)$_2$ 49.1; (phenyl-SO$_2$)$_2$Mg 58.0 | THF 10; H$_2$O 2 | MgBr$_2$·6H$_2$O 200 | Pt—Cu | 5-9 | 5.6 | benzothiazol-2-yl SSO$_2$-phenyl 83.3 (91.7) |
| 8 | (benzothiazolyl-S-)$_2$ 49.6; phenyl-SO$_2$NH$_4$ 59.2 | Acetone 10; H$_2$O 2 | MgBr$_2$·6H$_2$O 200 | Pt—Cu | 5-9 | 5.6 | benzothiazol-2-yl SSO$_2$-phenyl 81.6 (89.0) |
| 9 | (benzothiazolyl-S-)$_2$ 49.7; 4-CH$_3$-C$_6$H$_4$-SO$_2$Na 80.9 | THF 10; H$_2$O 2 | MgBr$_2$·6H$_2$O 200 | Pt—Cu | 5-9 | 4.2 | benzothiazol-2-yl SSO$_2$-C$_6$H$_4$-CH$_3$ 86.5 (90.0) |

TABLE 2-continued
| Ex. No. | Substrates mg | Solvents ml | Halogen salt mg | Electrode (+) (−) | Terminal Voltage V | Amount of Electricity F/mole | Product Yield mg (%) |
|---|---|---|---|---|---|---|---|
| 10 | 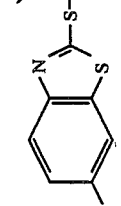 49.9 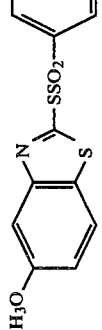 55.5 | THF 10 H₂O 2 | MgBr₂.6H₂O 200 | Pt—Cu | 5-9 | 4.1 | 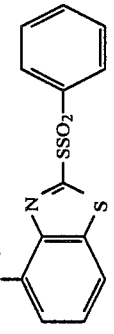 82.8 (93.0) |
| 11 | 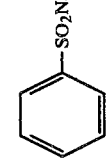 49.0 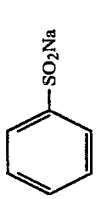 56.5 | THF 10 H₂O 2 | MgBr₂.6H₂O 200 | Pt—Cu | 5-9 | 4.1 | 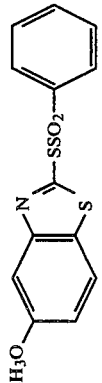 81.3 (93.0) |
| 12 | 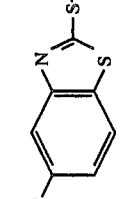 49.0 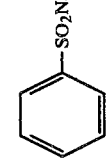 58.3 | THF 10 H₂O 2 | MgBr₂.6H₂O 200 | Pt—Cu | 5-9 | 4.5 | 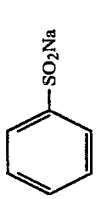 75.7 (90.1) |

TABLE 2-continued

| Ex. No. | Substrates mg | Solvents ml | Halogen salt mg | Electrode (+) (−) | Terminal Voltage V | Amount of Electricity F/mole | Product Yield mg (%) |
|---|---|---|---|---|---|---|---|
| 13 | [benzothiazolyl disulfide with NO₂] 59.1; PhSO₂Na 58.3 | THF 10; H₂O 2 | MgBr₂·6H₂O 200 | Pt—Cu | 5-9 | 4.5 | [6-nitro-2-(phenylsulfonylthio)benzothiazole] 81.8 (83.0) |
| 14 | [benzothiazolyl disulfide with Cl] 56.1; PhSO₂Na 58.3 | THF 10; H₂O 2 | MgBr₂·6H₂O 200 | Pt—Cu | 5-9 | 4.5 | [5-chloro-2-(phenylsulfonylthio)benzothiazole] 81.2 (85.0) |
| 15 | [benzothiazolyl disulfide] 49.1; 4-Br-C₆H₄SO₂Na 86.3 | THF 10; H₂O 2 | MgBr₂·6H₂O 200 | Pt—Cu | 5-9 | 4.5 | [2-(4-bromophenylsulfonylthio)benzothiazole] 98.2 (86.0) |

TABLE 2-continued

| Ex. No. | Substrates mg | Solvents ml | Halogen salt mg | Electrode (+) (−) | Terminal Voltage V | Amount of Electricity F/mole | Product Yield mg (%) |
|---|---|---|---|---|---|---|---|
| 16 | benzothiazole-SH 49.5; PhSO₂Na 56.8 | Diethylether 10; H₂O 2 | (CH₃)₄NBr 105 | Pt—Cu | 5–9 | 2.8 | benzothiazole-SSO₂Ph 81.5 (89.6) |
| 17 | benzothiazole-SNa 56.1; PhSO₂Na 57.1 | Acetonitrile 10; H₂O 2 | FeCl₃·4H₂O 160 | C—Ti | 5–9 | 2.9 | benzothiazole-SSO₂Ph 78.5 (86.1) |
| 18 | (benzothiazole-S)₂ 49.2; PhSO₂Na 58.1 | Ethylacetate 10; H₂O 2 | CuCl₂ 92 | Pt—C | 5–9 | 3.9 | benzothiazole-SSO₂Ph 81.2 (89.2) |
| 19 | (benzothiazole-S)₂ 49.2 | Dioxane 8; Ethanol 2; H₂O 2 | MgBr₂·6H₂O 200 | C-stainless steel | 5–9 | 3.8 | benzothiazole-SSO₂Ph 83.6 (91.9) |

TABLE 2-continued

| Ex. No. | Substrates mg | Solvents ml | Halogen salt mg | Electrode (+) (−) | Terminal Voltage V | Amount of Electricity F/mole | Product Yield mg (%) |
|---|---|---|---|---|---|---|---|
| 20 | PhSO₂Na 58.1; (benzothiazolyl-S)₂ 49.2 | Dichloromethane 10; H₂O 2 | MgBr₂·6H₂O 200 | Pt—Ni | 5-9 | 3.4 | benzothiazolyl-SSO₂-Ph 82.5 (90.7) |
| 21 | PhSO₂Na 58.1; (benzothiazolyl-S)₂ 49.2 | Chlorobenzene 10; H₂O 2 | MgBr₂·6H₂O 200 | Pt—Cu | 5-9 | 3.3 | benzothiazolyl-SSO₂-Ph 81.3 (89.4) |
| 22 | 4-CH₃O-C₆H₄-SO₂Na 67.2; (benzothiazolyl-S)₂ 49.3 | THF 10; H₂O 2 | MgBr₂·6H₂O 200 | Pt—Cu | 5-9 | 3.5 | benzothiazolyl-SSO₂-C₆H₄-OCH₃ 90.3 (90.2) |

| Ex. No. | Substrates mg | Solvents ml | Halogen salt mg | Electrode (+) (−) | Terminal Voltage V | Amount of Electricity F/mole | Product Yield mg (%) |
|---|---|---|---|---|---|---|---|
| 23 | 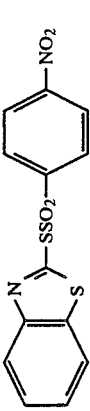 49.2<br><br>72.3 | THF 10<br>H$_2$O 2 | MgBr$_2$·6H$_2$O 200 | Pt—Cu | 5-9 | 3.6 | 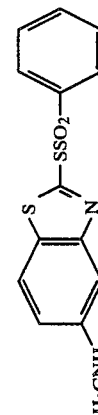 90.8 (87.0) |
| 24 | 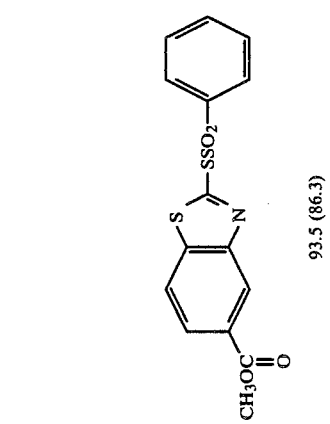 66.5<br><br>57.8 | THF 10<br>H$_2$O 2 | MgBr$_2$·6H$_2$O 200 | Pt—Cu | 5-9 | 3.1 | 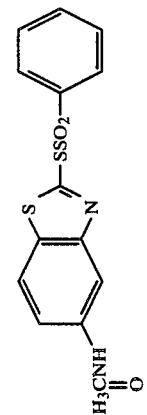 93.5 (86.3) |
| 25 | 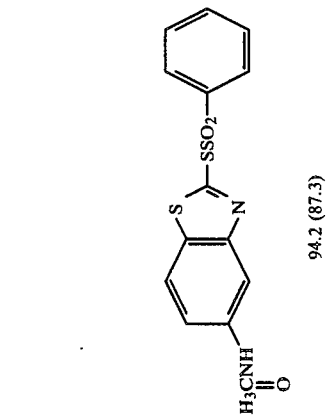 66.1<br><br>57.9 | THF 10<br>H$_2$O 2 | MgBr$_2$·6H$_2$O 200 | Pt—Cu | 5-9 | 3.3 | 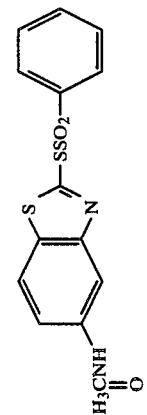 94.2 (87.3) |

TABLE 3

| Example | Product | NMR Spectrum δ (ppm), in CDCl$_3$ |
|---|---|---|
| 7, 8 | benzothiazole-2-S-SO$_2$-phenyl | 7.1–8.1 (9H, m) |
| 9 | benzothiazole-2-S-SO$_2$-C$_6$H$_4$-CH$_3$ | 2.41 (3H, S)<br>7.0–8.1 (8H, m) |
| 10 | 4-CH$_3$-benzothiazole-2-S-SO$_2$-phenyl | 2.59 (3H, S)<br>7.2–7.9 (8H, m) |
| 11 | 6-CH$_3$-benzothiazole-2-S-SO$_2$-phenyl | 2.48 (3H, S)<br>7.1–8.0 (8H, m) |
| 12 | 5-CH$_3$O-benzothiazole-2-S-SO$_2$-phenyl | 3.81 (3H, S)<br>6.9–7.8 (8H, m) |
| 13 | 6-NO$_2$-benzothiazole-2-S-SO$_2$-phenyl | 7.4–8.0 (5H, m)<br>8.07 (1H, d, J = 9Hz)<br>8.35 (1H, d.d, J = 9Hz, 2Hz)<br>8.77 (1H, d, J = 2Hz) |
| 14 | 5-Cl-benzothiazole-2-S-SO$_2$-phenyl | 7.2–8.4 (8H, m) |
| 16–21 | benzothiazole-2-S-SO$_2$-phenyl | 7.1–8.1 (9H, m) |

I claim:

1. A process for preparing a thiosulfonate derivative represented by the formula $$R^2SO_2SR^1 \quad (III)$$

wherein $R^1$ is substituted or unsubstituted 2-benzothiazolyl, and $R^2$ is substituted or unsubstituted phenyl, the process being characterized in that a compound represented by the formula $$R^1SX \quad (I)$$

wherein $R^1$ is as defined above, and X is hydrogen, alkali metal or $SR^1$, and a sulfinic acid or a salt thereof represented by the formula $$R^2SO_2Y \quad (II)$$

wherein $R^2$ is as defined above, and Y is a hydrogen atom, alkali metal atom, alkaline earth metal atom or quaternary ammonium are subjected to an electrolytic reaction in a mixture of water and an organic solvent in the presence of a halogen salt.

2. A process as defined in claim 1 wherein $R^1$ is unsubstituted 2-benzothiazolyl or 2-benzothiazolyl substituted with C$_1$–C$_4$ alkyl, C$_1$–C$_4$ alkoxyl, nitro, hydroxyl, C$_2$–C$_4$ alkanoyloxy, C$_2$–C$_4$ alkoxycarbonyl, amino, C$_2$–C$_5$ alkylcarbonylamino or halogen.

3. A process as defined in claim 1 wherein $R^2$ is unsubstituted phenyl or phenyl substituted with C$_1$–C$_4$ alkyl, C$_1$–C$_4$ alkoxyl, nitro, hydroxyl, C$_2$–C$_4$ alkanoyloxy, C$_2$–C$_4$ alkoxycarbonyl, amino, C$_2$–C$_5$ alkylcarbonylamino or halogen.

4. A process as defined in claim 1 wherein the compound of the formula (II) is used in an amount of at least about 1 equivalent based on the compound of the formula (I).

5. A process as defined in claim 1 wherein the organic solvent is at least one solvent selected from the group consisting of di(C$_1$–C$_4$ alkyl)ethers, cyclic ethers, di(C$_1$–C$_4$ alkyl)ketones, C$_2$–C$_4$ nitriles, C$_1$–C$_4$ aliphatic alcohols, esters of C$_1$–C$_4$ fatty acids with C$_1$–C$_4$ aliphatic alcohols, C$_1$–C$_4$ halogenated hydrocarbons and halogenobenzenes.

6. A process as defined in claim 1 wherein the organic solvent is used in an amount of about 5 to about 500 times the amount by weight of the compound of the formula (I).

7. A process as defined in claim 1 wherein the water is used in an amount of about 1 to about 50% by weight of the organic solvent.

8. A process as defined in claim 1 wherein the halogen salt is an alkali metal halide, alkaline earth metal halide, heavy metal halide or quaternary ammonium halide.

9. A process as defined in claim 1 wherein the halogen salt is used in an amount of about 0.01 to about 10 moles per mole of the compound of the formula (I).

10. A process as defined in claim 1 wherein the electrolytic reaction is conducted at a constant current density of about 1 to about 500 mA/cm$^2$.

11. A process as defined in claim 1 wherein the electrolytic reaction is conducted by applying about 1 to about 20 F of electricity per mole of the compound of the formula (I).

12. A process as defined in claim 1 wherein the electrolytic reaction is conducted at a temperature of about $-20°$ to about $+100°$ C.

* * * * *